United States Patent [19]

Barberet et al.

[11] Patent Number: Plant 5,512

[45] Date of Patent: Jul. 9, 1985

[54] CARNATION NAMED LONPILEM

[75] Inventors: Nicole Barberet; Yves Ducloux, both of Antibes, France

[73] Assignee: Laboratoire de Physiologie Vegetale de la Londe SCS Barberet and Ducloux, La Londe, France

[21] Appl. No.: 517,213

[22] Filed: Jul. 25, 1983

[51] Int. Cl.[3] ..... A01H 5/00

[52] U.S. Cl. ..... Plt./71

[58] Field of Search ..... Plt./71

*Primary Examiner*—Robert E. Bagwill

*Attorney, Agent, or Firm*—Chas. W. Rummler

[57] ABSTRACT

A new standard carnation cultivar particularly distinguished by the Dawn pink to Venetian pink coloration of its medium sized flowers which are borne on long, strong, straight stems and which bloom profusely during the recurrent blooming seasons of Spring and Fall. This plant has a vigorous, upright and very tall growth habit with moderately abundant foliage and a height averaging about 127 cm. at eight months which provides extra long flower stems making it particularly advantageous for use in vase arrangements.

1 Drawing Figure

BACKGROUND OF THE NEW PLANT

Our new carnation cultivar is the result of breeding efforts carried on by us at La Londe, Les Maures, France, since 1980, this new plant originating as a seedling produced from our crossing of selected and individually identified plants growing among our stock of plants maintained at La Londe for breeding purposes. This particular seedling was selected by us for propagation and test because of its very unusual combination of light pink colors and its very favorable and tall growth habit. This discovery plant was reproduced by us at La Londe, by means of cuttings of the parent, and the result of that propagation effort appearing to be very favorable with respect to retention of the novel characteristics of the parent plant, we continued such propagation through several successive generations and established that the novel and distinctive characteristics of the discovery plant are fully retained from generation to generation and appear to be firmly fixed.

DESCRIPTION OF THE DRAWING

Our new carnation cultivar is illustrated by the accompanying photographic drawing which shows, in full color, an arrangement of buds and flowers in various stages of opening, the colors shown being as nearly true to those specified herein as is reasonably possible to obtain by conventional photographic procedures.

DESCRIPTION OF THE NEW PLANT

The following is a detailed description of our new carnation discovery based upon observations of greenhouse grown plants at La Londe, France, in the Spring of 1983, the color designations being specified according to The R.H.S. Colour Chart published by The Royal Horticultural Society of London, England.

THE PLANT

Origin: Seedling.

Parentage:

*Seed parent.*—Stock Plant No. 83 91 P.

*Pollen parent.*—Stock Plant No. 76 P 11. These unnamed varieties are individually identified in our permanent records and are maintained for breeding purposes in our collection of carnation plants at La Londe, France.

Classification:

*Botanic.—Dianthus caryophyllus.*

*Commercial.*—Standard Carnation.

Form: Tall, erect bush with at least four stems emitted near the ground.

Height: About 127 cm. in average at eight months.

Main stem:

*Length.*—Less than 15 cm. due to pinching.

Branching character: Only a few branches.

Growth habit: Vigorous, upright, strong and rigid.

Foliage:

*Quantity.*—Moderately abundant.

*Number of leaves.*—More than 120.

*Leaf size.*—Averaging about 14.7 cm. long and 1 cm. wide at the seventh node.

*Leaf shape.*—Linear with rolled margin.

*Texture.*—Leathery.

*Color.*—Upper side — 189A. Under side — 189A.

*Ribs and veins.*—Hardly noticeable.

*Rachis.*—Hardly noticeable.

THE BUD

Size: Medium.

*Diameter.*—About 2.2 cm. in average.

*Length.*—About 3.4 cm. in average.

Form: Ovoid.

Opening rate: About normal for carnations.

Color of petals:

*When sepals first divide.*—49D-C.

*When petals begin to unfurl.*—49A/B.

Sepals:

*Shape.*—Joined at lower part, the upper part being of acute character with sharp pointed apex. The sepals are hooded over the bud and stand up when the flower opens.

*Color.*—Inside — Greenish white. Outside — 144C with traces of 137D.

Calyx:

*Size.*—Large.

*Shape.*—Bell-shaped and of medium length.

*Splitting.*—The calyx does not split.

*Aspect.*—Smooth.

Flower stem:

*Length.*—About 75 cm.
*Character.*—Erect and rather rigid.
*Color.*—189A.

THE FLOWER

Blooming habit: Recurrent, blooming profusely during midseason of Spring and Fall.
Size of bloom: Medium.
*Diameter.*—About 8.7 cm. in average.
*Depth.*—About 6 cm. in average.
Borne: Singly.
Shape:
*When bloom first opens.*—High centered.
*When bloom matures.*—Dome-shaped.
Petalage:
*Number of petals.*—Averaging about 59.
*Arrangement.*—Imbricated.
*Form.*—Fan-shaped with dentate margins having rounded tips.
*Texture.*—Soft.
*Appearance.*—Satiny.
*Color.*—Outer Petal: Body — Dawn Pink 49A/B and Venetian Pink 49C. Base — Greenish white. Reverse side — 49B and 49D. Inside Petal: Body — 49A/B and 49C. Base — Greenish white. Reverse side — 49B and 49D.
Flower stem:
*Length.*—About 74 cm. in average (cut at tenth node).
*Character.*—Upright and of good strength.
*Color.*—189A.
Fragrance: Fragrance is present.

Persistence: The flower petals hang on and dry.
Lasting quality:
*As cut flower.*—At least ten days with vase keeping.
Disease resistance: Resistant to *Fusarium oxysporum* as observed INRA, Antibes, Alpes-Maritimes, France.

REPRODUCTIVE ORGANS

Stamens:
*Number.*—3 To 11.
*Arrangement.*—Around the pistils.
*Anthers.*—Size: Less than 4 mm. Color: Whitish.
*Filaments.*—Length: Less than 4 mm. Color: Whitish.
Pistils:
*Number.*—Two.
*Styles.*—Color — White.
*Stigmas.*—Color — Pinkish white.
Character of ovaries: Cone-shaped and not ribbed.

This variety most nearly resembles Barlo II (U.S. Plant Pat. No. 3,406) and differs by having a somewhat darker color, much less splitting of flowers, less branched stems, and being resistant to *Fusarium oxysporum.*

We claim:

1. The new and distinct carnation cultivar, substantially as herein shown and described, characterized by the pink coloration of its medium sized blooms which are carried on long, strong, stiff stems; and by its advantageous tall growth habit, and its abundant production of flowers during its Spring and Fall blooming seasons.

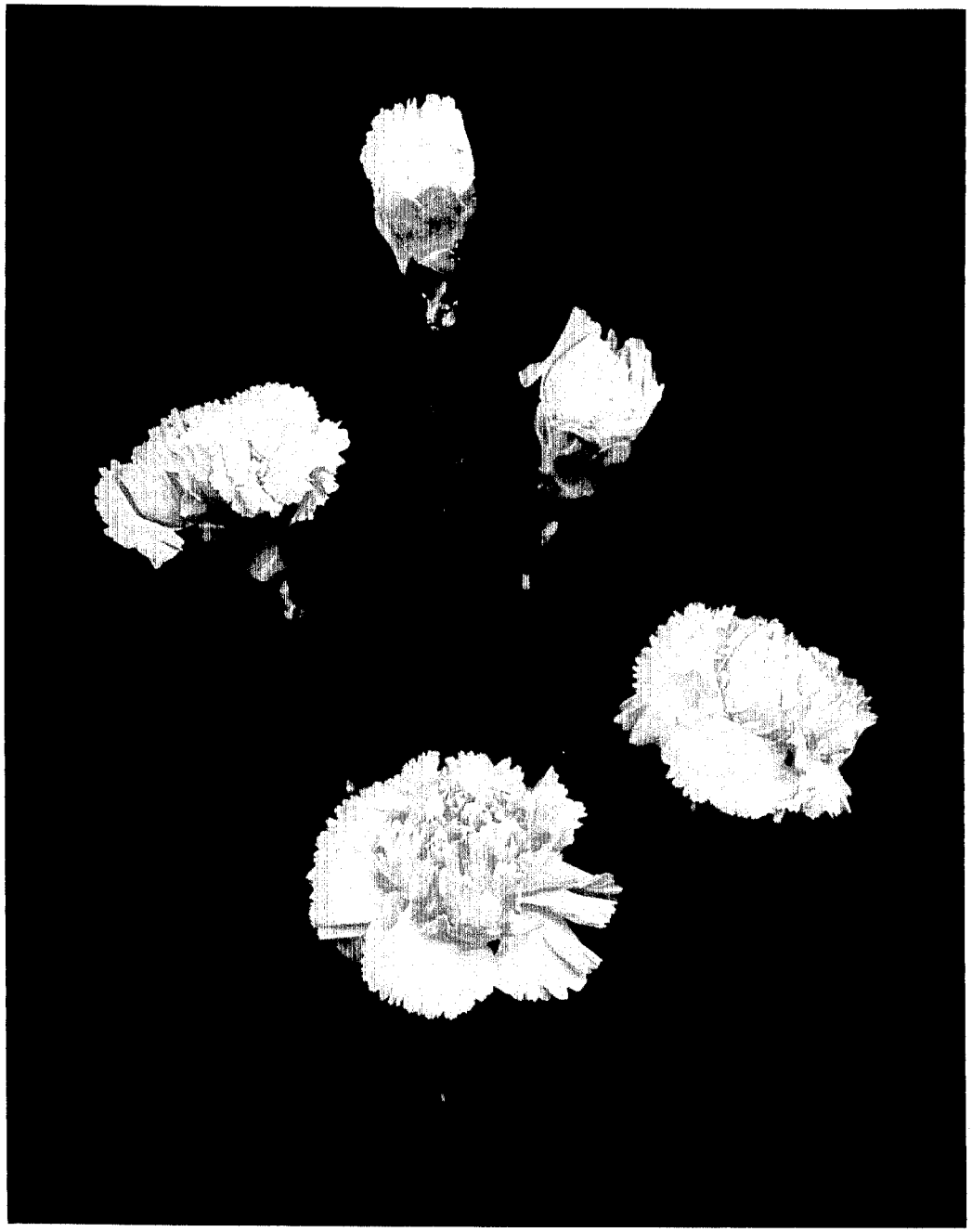

* * * * *